US009994814B2

(12) United States Patent
Giampapa

(10) Patent No.: US 9,994,814 B2
(45) Date of Patent: Jun. 12, 2018

(54) METHOD FOR CELLULAR RESTORATION

(71) Applicant: Advanced Regen Medical Technologies, LLC, Houston, TX (US)

(72) Inventor: Vincent C. Giampapa, Montclair, NJ (US)

(73) Assignee: Advanced Regen Medical Technologies, LLC, Houston, TX (US)

( * ) Notice: Subject to any disclaimer, the term of this patent is extended or adjusted under 35 U.S.C. 154(b) by 0 days. days.

(21) Appl. No.: 14/889,942

(22) PCT Filed: Apr. 9, 2014

(86) PCT No.: PCT/US2014/033564
§ 371 (c)(1),
(2) Date: Nov. 9, 2015

(87) PCT Pub. No.: WO2014/169077
PCT Pub. Date: Oct. 16, 2014

(65) Prior Publication Data
US 2016/0145571 A1     May 26, 2016

Related U.S. Application Data

(60) Provisional application No. 61/811,358, filed on Apr. 12, 2013, provisional application No. 61/810,182, filed on Apr. 9, 2013.

(51) Int. Cl.
| *C12N 5/00* | (2006.01) |
| *C12N 5/074* | (2010.01) |
| *A61K 45/06* | (2006.01) |
| *A61K 35/545* | (2015.01) |
| *A61K 35/28* | (2015.01) |

(52) U.S. Cl.
CPC ............ *C12N 5/0607* (2013.01); *A61K 35/28* (2013.01); *A61K 35/545* (2013.01); *A61K 45/06* (2013.01); *C12N 2502/03* (2013.01)

(58) Field of Classification Search
None
See application file for complete search history.

(56) References Cited

U.S. PATENT DOCUMENTS

| 8,257,973 B2 | 9/2012 | Park et al. |
| 2005/0158285 A1 | 7/2005 | Giampapa |
| 2007/0196918 A1 | 8/2007 | Sayre et al. |
| 2013/0302285 A1* | 11/2013 | Fong ................... C12N 5/0668 424/93.7 |

FOREIGN PATENT DOCUMENTS

| CA | 2845280 | 2/2012 |
| KR | 10-2008-0049917 | 6/2008 |
| WO | 2007109223 | 9/2007 |
| WO | 2008066330 | 6/2008 |
| WO | 2009011546 | 1/2009 |
| WO | 2013134513 | 9/2013 |
| WO | 2015095794 A1 | 6/2015 |

OTHER PUBLICATIONS

Extended European Search Report for Patent Application No. 14782619.2-1466, dated Oct. 26, 2016.
Sun Yun et al: "Rescuing replication and osteogenesis of aged mesenchymal stem cells by exposure to a young extracellular matrix", Faseb Journal, vol. 25, No. 5, May 2011.
McCullagh, Karl J A: "Can a young muscle's stem cell secretome prolong our lives?", Stem Cell Research & Therapy, vol. 3, May 2012.
Ratajczak M Z et al: "Pivotal role of paracrine effects in stem cell therapies in regenerative medicine: can we translate stem cell-secreted paracrine factors and microvesicles into better therapeutic strategies?", Leukemia (Basingstoke), vol. 26, No. 6, Jun. 2012.
International Search Report and Written Opinion application No. PCT/US2014/033564 dated Aug. 26, 2014.
Office Action for Canadian Patent Application No. 2,911,692, dated Oct. 17, 2016.
Tatsumi, Kimiko et al: "Granulocyte-Colony Stimulation Factor Increases Donor Mesenchymal Stem Cells in Bone Marrow and Their Mobilization Into Peripheral Circulation but Does Not Repair Dystrophic Heart After Bone Marrow Transplantation", Circ J, 2008.
Office Action for Korean Patent Application No. 10-2015-7032122, dated Feb. 20, 2016.
Lavasani, Mitra, et al., "Muscle-derived stem/ progenitor cell dysfunction limits healthspan and lifespan in a murine progeria model," Nature Communications, Jan. 3, 2012, pp. 1-12, vol. 3, No. 608, Macmillan Publishers Limited.
Foreign Communication from a related Application—Examination Report of European Patent Application No. 14782619.2 dated Nov. 23, 2017, 6 pages.
Foreign Communication from a related Application—Examination Report of Canadian Patent Application No. 2,911,692 dated Oct. 10, 2017, 5 pages.
Foreign Communication from a related Application—Examination Report and of Korean Patent Application No. 10-2015-7032122 dated Sep. 7, 2017 with translation, 17 pages.
Foreign Communication from a related Application—Examination Report and of Korean Patent Application No. 10-2015-7032122 dated Nov. 16, 2017 with translation, 14 pages.
Foreign Communication from a related Application—Examination Report of Korean Patent Application No. 10-2015-7032122 dated Mar. 13, 2017 with translation, 20 pages.

* cited by examiner

*Primary Examiner* — Blaine Lankford
(74) *Attorney, Agent, or Firm* — Conley Rose, P.C.; Rodney B. Carroll

(57) ABSTRACT

A method comprising obtaining a donor composition from a donor subject wherein the donor composition comprises a plurality of adult stem cell types; obtaining a receiver composition from a receiver subject wherein the receiver composition comprises a plurality of adult stem cell types; and co-culturing the donor composition and receiver composition wherein co-culturing comprises contacting the receiver composition a cell-free portion of the donor composition to produce a restored composition. Pharmaceutical compositions comprising a restored composition.

24 Claims, 13 Drawing Sheets

METHOD FOR CELLULAR RESTORATION

TECHNICAL FIELD

The present disclosure generally relates to compositions and methods for improving the cellular health of a subject. More specifically this disclosure relates to compositions and methods for cellular restoration.

BACKGROUND

Aging is an important risk factor for most chronic diseases and is the primary factor for the majority of morbidity and health care expenditures in developed nations. Decreased cellular function associated with cellular senescence results in the disorders and dysfunctions typically associated with aging mammalian cells. A potent inducer of cellular senescence is (epi)genomic stress, which can result from direct DNA damage, dysfunctional telomeres, disrupted chromatin or strong mitogenic signals. Additionally cellular senescence can cause chronic inflammation through the senescence-associated secretory factors (SASF).

There exists an ongoing need for compositions and methods that improve cellular functions that have been negatively impacted due to one or mechanisms associated with cellular senescence. Further there exists an ongoing need for compositions and methods to improve the cellular health of a subject.

SUMMARY

Disclosed herein is a method comprising obtaining a donor composition from a donor subject wherein the donor composition comprises a plurality of adult stem cell types; obtaining a receiver composition from a receiver subject wherein the receiver composition comprises a plurality of adult stem cell types; and co-culturing the donor composition and receiver composition wherein co-culturing comprises contacting the receiver composition a cell-free portion of the donor composition to produce a restored composition.

Also disclosed herein are pharmaceutical compositions comprising a restored composition.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
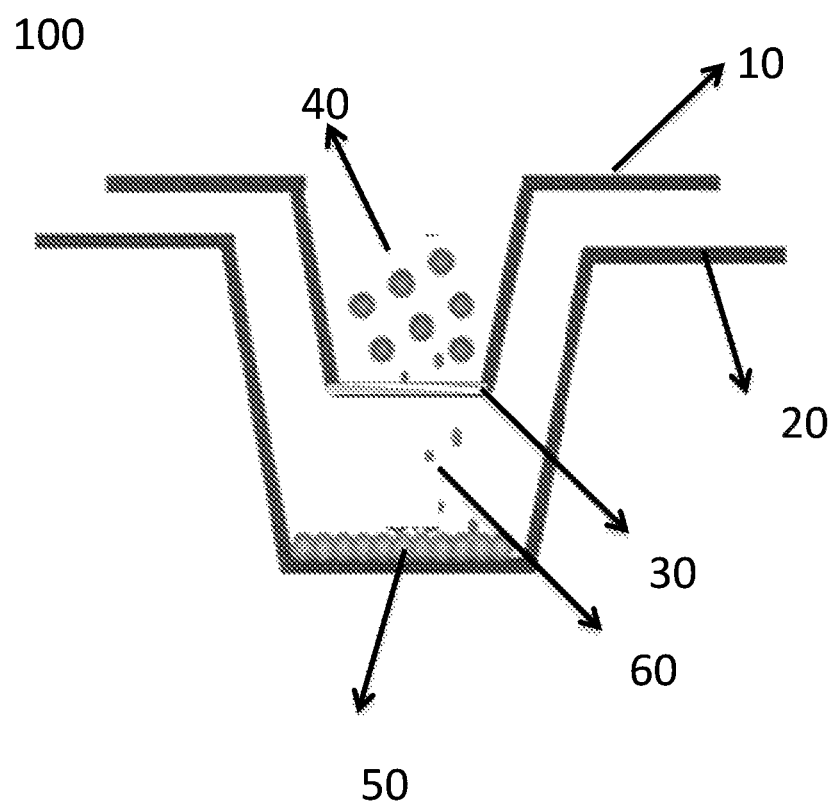
FIG. 1 is a depiction of an embodiment of a restoration method disclosed herein.
Figure 2A:
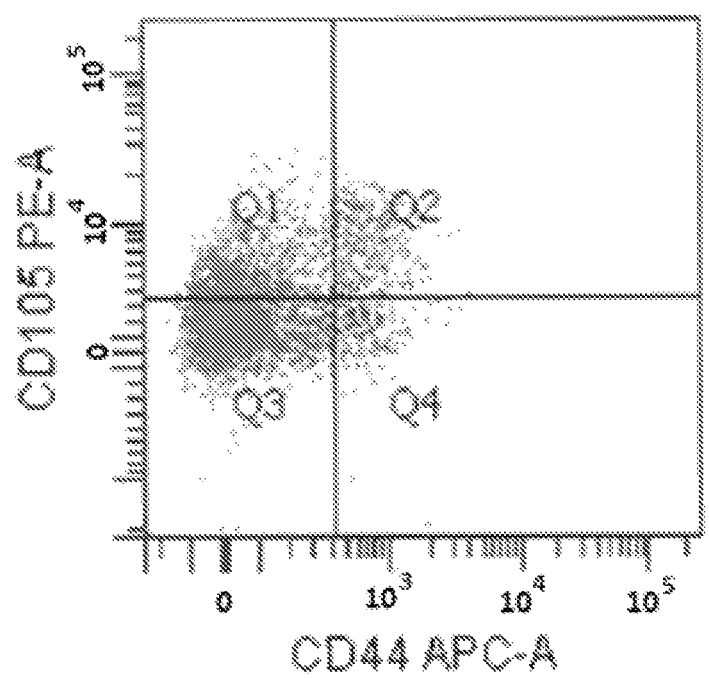
FIG. 2a depicts the results of flow cytometry for a sample from Example 1.
Figure 2B:
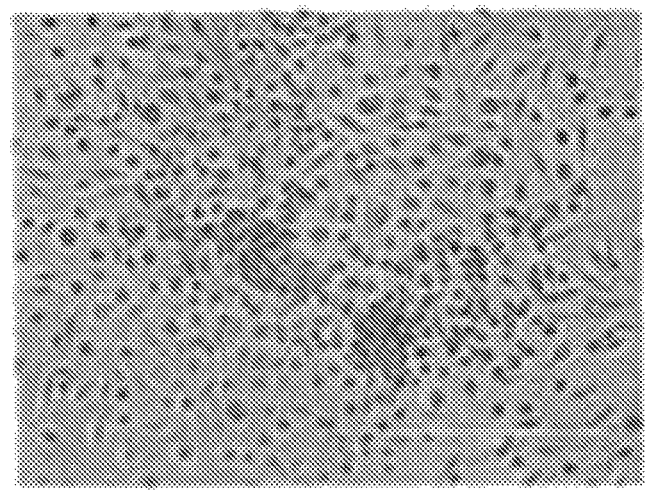
FIG. 2b depicts the results of microscopy for a sample from Example 1.
Figure 3:
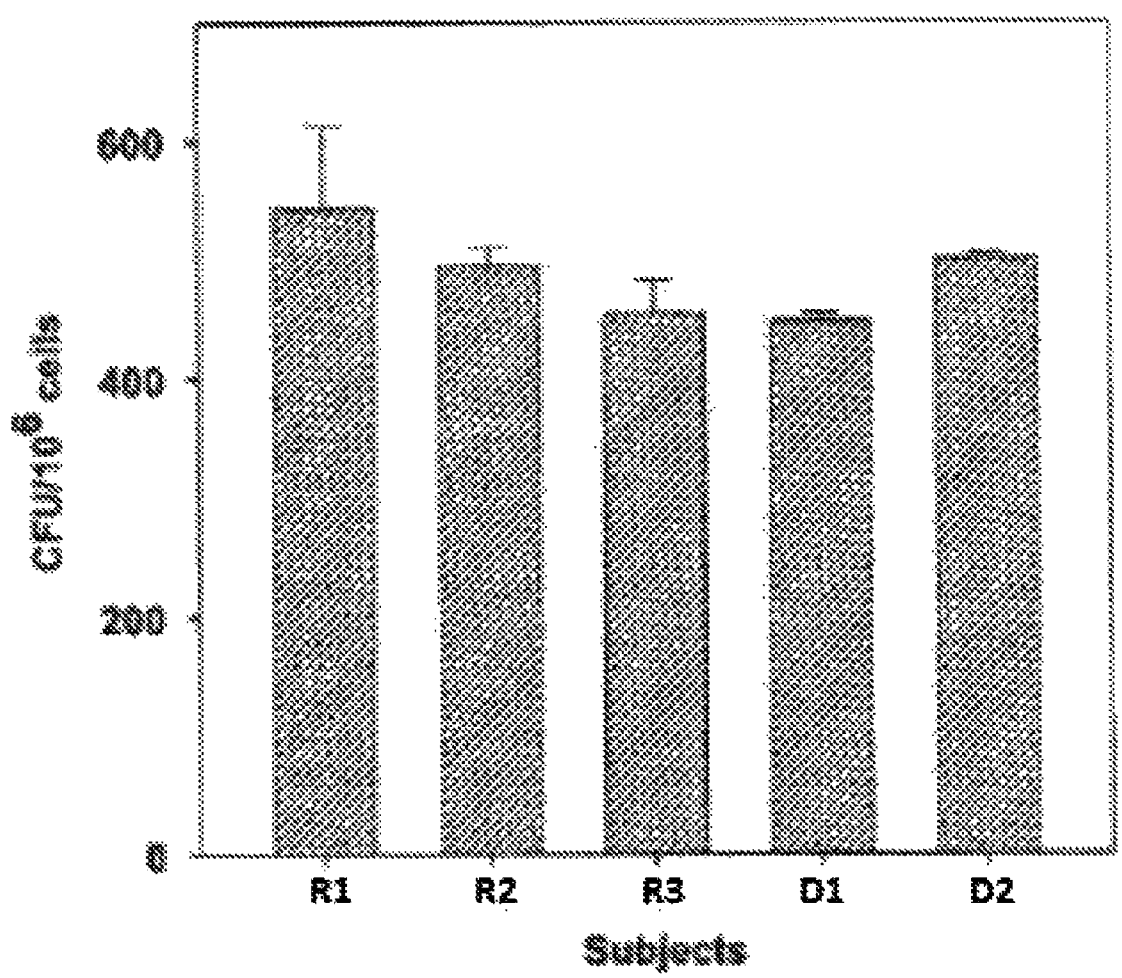
FIG. 3 depicts a plot of the number of colony forming units per one million cells for the subjects of Example 1.
Figure 4A:
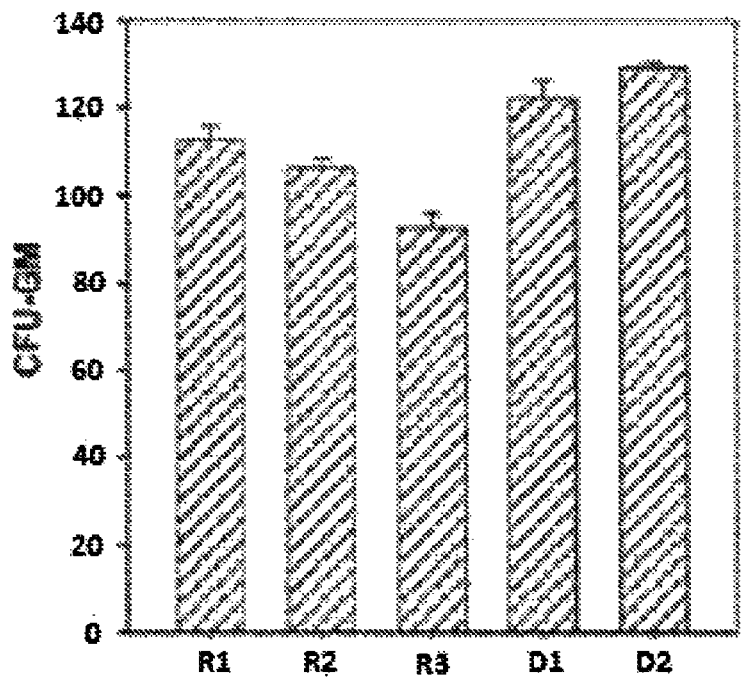
FIG. 4a depicts a plot of the colony forming units (CFU) as part of the baseline (day 0) clonogenic assay for the subjects from Example 1.
Figure 4B:
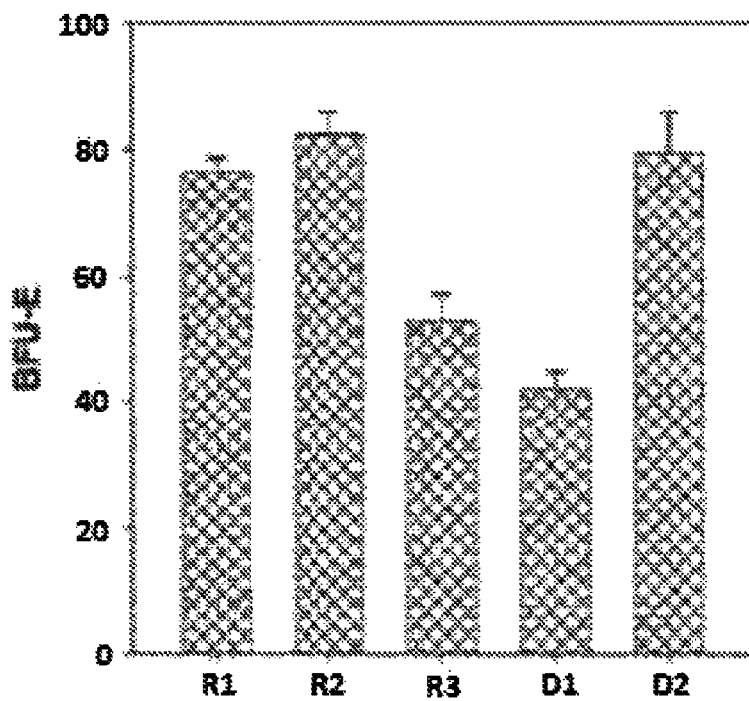
FIG. 4b depicts a plot of the burst forming erythroids as part of the baseline (day 0) clonogenic assay for the subjects from Example 1.
Figure 5A:
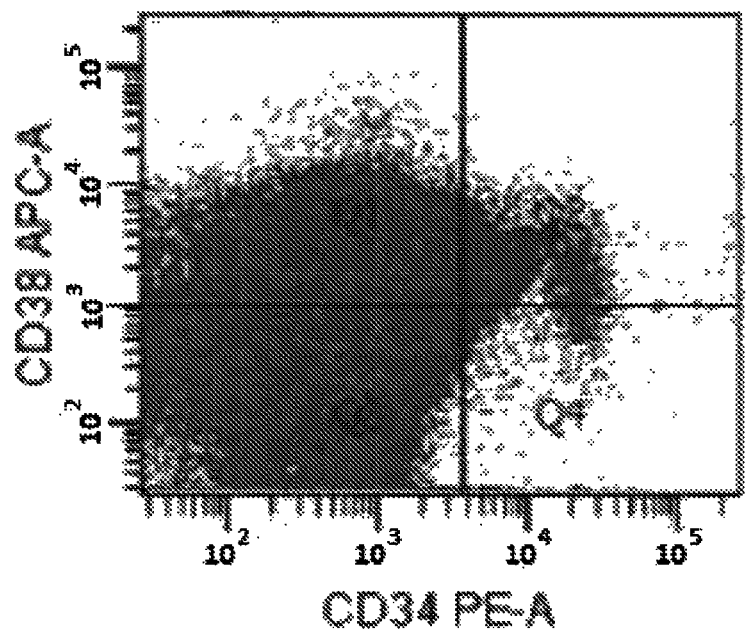
FIG. 5a depicts flow cytometry results for a sample from Example 1 based on CD34 PE-A, and CD38 APC-A.
Figure 5B:
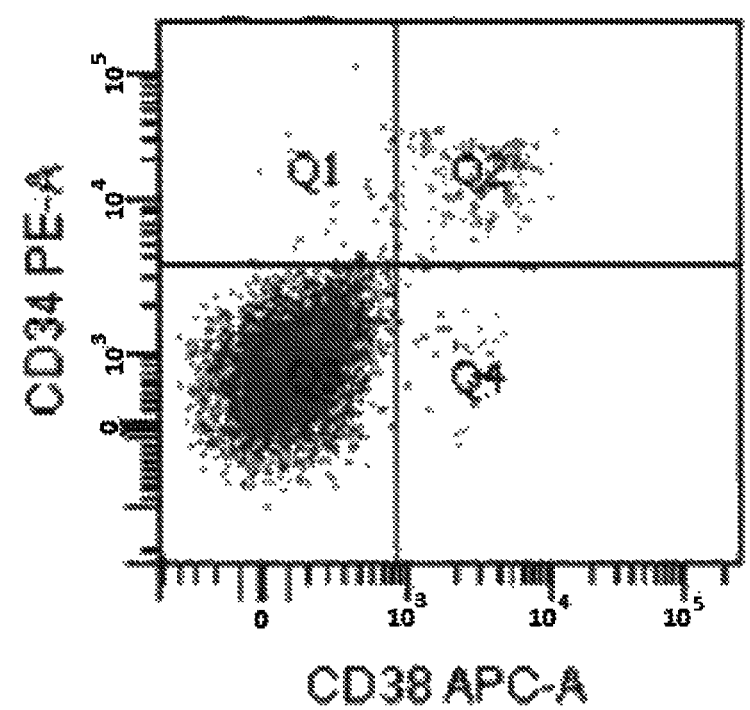
FIG. 5b depicts flow cytometry results for a sample from Example 1 based on CD38 APC-A, and CD34 PE-A.

Disclosed herein are compositions and methods for improving the cellular health of a subject. The term "subject," as used herein, comprises any and all organisms and includes the term "patient." In an embodiment the subject is a human or any other animal. Herein the term "cellular health" refers to improvements in parameters of cellular function that result in a perceived and/or quantifiable improvement in the subject's general health. "Treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted. Treatment also encompasses any pharmaceutical or medicinal use of the compositions herein. "Prophylactic" or "therapeutic" treatment refers to administration to the subject of one or more of the disclosed compositions. If it is administered prior to clinical manifestation of an unwanted condition (e.g., medical condition, disease, disorder, dysfunction) then the treatment is prophylactic, i.e., it protects the subject against developing the unwanted condition, whereas if administered after manifestation of the unwanted condition, the treatment is therapeutic (i.e., it is intended to diminish, ameliorate or maintain the existing unwanted condition or side effects therefrom).

In an embodiment, the subject is administered the compositions disclosed herein in a therapeutically effective amount and used for treating, preventing and/or ameliorating one or more symptoms of a medical condition, disorder, disease, or dysfunction. Hereinafter for simplicity the afflicted condition which has been used interchangeably with the terms medical condition, disorder, disease and dysfunction are collectively referred to as the "medical condition." As used herein, amelioration of the symptoms of the medical condition by administration of a particular composition of the type disclosed herein refers to any lessening, whether permanent or temporary, lasting or transient that can be attributed to or associated with administration of compositions of the type disclosed herein. As used herein, a "therapeutically effective amount" means a sufficient amount of the compositions disclosed herein to treat, prevent and/or ameliorate one or more symptoms of the medical condition. It also may include a safe and tolerable amount of the compositions disclosed herein, as based on industry and/or regulatory standards. As will be understood by the ordinarily skilled artisan an amount that proves to be a "therapeutically effective amount" in a given instance, for a particular subject, may not be effective for 100% of subjects similarly treated for the medical condition under consideration, even though such dosage is deemed a "therapeutically effective amount" by ordinarily skilled practitioners.

One or more compositions disclosed herein may comprise cells and/or cellular material obtained from a human subject. Herein the term "cellular material" refers to materials derived from, secreted, and otherwise currently or previously associated with a cell. In an embodiment, a method of the present disclosure comprises contacting a donor composition with a receiver composition to produce a restored composition where both the donor and receiver compositions comprise cells and/or cellular material. The restored composition may be administered to a subject in need thereof.

In an embodiment the donor composition is provided by a donor subject while the receiver composition is provided by a receiver subject. In some embodiments the donor subject and receiver subject are the same. Alternatively, the donor subject and receiver subject are different. In an embodiment, the donor subject is chosen such that the difference in the age of the donor subject, designated x, and the age of the receiver subject, designated y, is greater than about 5 years, alternatively, greater than about 10 years, alternatively greater than about 15 years, alternatively greater than about 20 years, alternatively greater than about 25 years, or alternatively greater than about 30 years where y is greater than x. In an embodiment, the donor subject is chosen such that the difference in the age of the donor subject, x, and the age of the receiver subject, y, is from about 5 years to about 75 years, alternatively from about 10 years to about 60 years, alternatively from about 15 years to about 50 years, alternatively from about 20 years to about 40 years, or alternatively from about 20 years to about 30 years where y is greater than x.

In an embodiment, the donor subject and receiver subject are related by consanguinity. Alternatively, the donor subject and receiver subject are not related. In an embodiment, the receiver subject has a medical condition that is absent from or undiagnosed in the donor subject. In either embodiment, the donor subject and the receiver subject are adults which are humans that have reached sexual maturity. In an alternative embodiment, the donor subject is an adult.

In an embodiment, the donor composition, receiver composition or both are obtained from a subject who has undergone a Stage B preparation. In some embodiments, the donor composition, receiver composition, or both are obtained from a subject who has undergone a Stage A preparation and a Stage B preparation.

In an embodiment, the donor composition, the receiver composition or both are obtained from a subject that has undergone a Stage A preparation. Herein a Stage A preparation of a subject comprises the utilization of methods and/or compositions to improve the subject's general cellular health prior to obtaining a composition (i.e., donor composition or receiver composition) from the subject. An example of a methodology to improve the subject's general cellular health includes the administration of one or more metabolic mediators to the subject. In such embodiments, the subject may be administered a plurality of metabolic mediators prior to obtaining one or more compositions of the type disclosed herein from the subject. Such metabolic mediators may be administered via any suitable methodology and may comprise a plurality of compounds which when normally present in insufficient amounts in the subject is detrimental to the physiological and/or psychological state of the subject. Other metabolic mediators may comprise compounds able to beneficially impact the physiological and/or psychological state of the subject. In an embodiment, the metabolic mediator comprises a nutraceutical. A non-limiting example of a nutraceutical suitable for use in the Stage A preparation of a subject is commercially available as EVERYCELL®, HEALTHYCELL, or HEALTHYCELL PLUS from Cell Health Institute. Additional compositions suitable for use metabolic mediators in the present disclosure are described in U.S. patent application Ser. No. 13/573,386 entitled "Dietary Supplement System for Multifunctional Anti-Aging Management and Method of Use" which is incorporated by reference herein in its entirety.

Another example of a methodology suitable for use in Stage A preparation of a subject comprises the administration of one or more pulsed electromagnetic fields (PEMF) to at least a portion of the subject's body prior and/or subsequent to obtaining a composition of the type disclosed herein. PEMF may be used to enhance the homing, engraftment, and/or differentiation of the adult stem cells.

Stage A preparation of a subject may be carried out for some period of time prior and/or subsequent to obtaining a composition of the type disclosed herein from the subject. For example, Stage A preparation may comprise administration of a nutraceutical to the subject at a particular dosage (e.g., 500 mg, twice daily) for a period of time greater than about 48 hours prior to obtaining a composition of the type disclosed herein from the subject. Alternatively, the nutraceutical is administered for a time period of from about 48 hours to about 1 year prior to obtaining a composition of the type disclosed herein from the subject, alternatively for from about 1 week to about 9 months, or alternatively for from about 1 month to about 6 months.

In an embodiment, the donor composition, the receiver composition, or both are obtained from a subject that has undergone a Stage B preparation. In an embodiment, during a Stage B preparation the subject (donor and/or receiver) undergoes at least one process for mobilizing the subject's stem cells. Herein "stem cells" are given their usual meaning which generally refers to cells, which are not terminally differentiated and are therefore able to produce cells of other types. Stem cells are divided into three types, including totipotent, pluripotent, and multipotent. "Totipotent stem cells" can grow and differentiate into any cell in the body, and thus can grow into an entire organism. These cells are not capable of self-renewal. In mammals, only the zygote and early embryonic cells are totipotent. "Pluripotent stem cells" are true stem cells, with the potential to make any differentiated cell in the body, but cannot contribute to making the extraembryonic membranes (which are derived from the trophoblast). "Multipotent stem cells" are clonal cells that self-renew as well as differentiate to regenerate adult tissues. "Multipotent stem cells" are also referred to as "unipotent" and can only become particular types of cells, such as blood cells or bone cells. The term "stem cells", as used herein, refers to pluripotent stem cells capable of self-renewal. In an embodiment, the donor and receiver compositions comprise adult stem cells and/or adult stem cell material which refer to stem cells or stem cell material that are not embryonic in origin or derived from embryos or fetal tissue. In an alternative embodiment, the donor composition comprises adult stem cells and/or adult stem cell material which refers to stem cells or stem cell material that are not embryonic in origin or derived from embryos or fetal tissue.

In an embodiment, the Stage B preparation comprise administering to a subject an effective amount of a mobilizer. A "mobilizer of hematopoietic stem cells or progenitor cells" or "mobilizer", (used interchangeably) as described herein refers to any compound, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. Such a "mobilizer" may increase the number of stem cells (e.g., hematopoietic stem cells or hematopoietic progenitor/precursor cells) in the peripheral blood, thus allowing for a more accessible source of stem cells for use in the methods disclosed herein. Any mobilizer suitable for increasing the number of stem cells available to be harvested in the subject and compatible with the other aspects of this disclosure may be utilized. In an embodiment the mobilizer is a cytokine such as granulocyte colony-stimulating factor (G-CSF). A commercial example of a mobilizer suitable for use in the present disclosure is NEUPOGEN® (filgrastim) which is a prescription medication used to treat neutropenia that is commercially available from Amgen.

Subsequent to administration of the mobilizer, and after a suitable time period has elapsed; a composition (e.g., donor composition or receiver composition) may be harvested from a subject's bone marrow. The time period between administration of the mobilizer to the subject and harvesting of the composition may be varied to meet one or more user and/or process goals. In an embodiment, the time period between administration of the mobilizer and harvesting of the composition may range from about 24 hours to about 10 days, alternatively from about 48 hours to about 7 days or alternatively from about 3 days to about 5 days.

In an embodiment, the composition is harvested from a subject using any suitable methodology, for example using an extracorporeal therapy such as apheresis. In such an embodiment, the composition may be harvested using intravenous needles located in a vein in each arm of a subject. Blood may be removed from a first vein, passed through an extracorporeal circuit that separates out the composition of interest and the remaining material may be returned to a second vein. For example, the composition may be harvested from the iliac crest of a subject. In such embodiments, bone marrow aspiration to obtain the composition may involve a healthcare provider locating the posterior iliac crest of the subject subsequent to carrying out standard precautions such as skin sterilization and the administration of a local anesthetic. A suitable needle with the stylet in place may be slowly advanced through the skin and subcutaneous tissue pointing towards the anterior superior iliac spine. Upon reaching the posterior iliac crest, the area may be penetrated by the needle until an adequate depth is reached. Once the needle is in place the stylet may be removed, a syringe attached, and the aspiration performed. In an embodiment a plurality of bone marrow aspirations are carried out in order to obtain some user and/or process desired number of cells in the composition.

In an embodiment, during and/or subsequent to Stage A and/or Stage B preparation of a subject, at least one physiological parameter of the subject may be monitored. For example, the subject's heart rate, blood pressure, temperature, and/or weight may be monitored for some period of time prior to and/or subsequent to Stage A and/or Stage B preparation of a subject. In an embodiment, the at least one physiological parameter may be utilized to identify appropriate times for obtaining a composition of the type disclosed herein from the subject.

In an embodiment, the compositions are obtained, or "harvested" when a user and/or process-desired number of stem cells have been mobilized to the peripheral blood. Any suitable methodology may be utilized to determine the number of mobilized stem cells such as for example blood CD34+ cell counting by flow cytometry.

In an embodiment, the donor composition, the receiver composition or both comprise a plurality of adult stem cell types including but not limited to mesenchymal stem cells, hematopoietic stem cells, early hematopoietic progenitor cells, late hematopoietic progenitor cells, endothelial progenitor cells or combinations thereof. Herein an "adult stem cell" refers to an undifferentiated (unspecialized) cell that occurs in a differentiated (specialized) tissue, renews itself, and becomes specialized to yield all of the specialized cell types of the tissue in which it is placed when transferred to the appropriate tissue. Adult stem cells are capable of making identical copies of themselves for the lifetime of the organism. This property is referred to as "self-renewal." Adult stem cells usually divide to generate progenitor or precursor cells, which then differentiate or develop into "mature" cell types that have characteristic shapes and specialized functions, e.g., muscle cell contraction or nerve cell signaling.

In an embodiment, the method disclosed herein further comprises subjecting the donor composition and/or receiver composition to one or more analytical methodologies for characterizing the composition. For example, the donor composition and/or receiver composition may be subjected to any suitable methodology for determining the number and type of cells present in the composition, for sorting the composition into particular cell types, for determining the viability of the cell, for determining the expression level of one or more genes or proteins in the compositions and the like. In an embodiment, the harvested cells may be subjected to one or more methodologies to characterize the cell types present. In some aspects, the harvested cells may be separated into cell types utilizing cell sorting techniques such as flow cytometry while the viability of the harvested cells may be assessed using methodologies such as clonogenic assays and trypan blue exclusion. In an embodiment, the harvested cells are greater than about 90% viable, alternatively greater than about 91, 92, 93, 94, 95, 96, or 97% viable.

In an embodiment, the method comprises subjecting the donor and/or receiver composition to one or more methodologies for characterizing the number of senescent and non-senescent cells in the composition. Cells that have exhausted their potential for growth are said to have undergone "senescence." Senescent cells acquire a large and flat cellular appearance, decrease contacts with other cells, and increase adhesion to the extracellular matrix. Molecularly, the cellular senescence program activates p53 and pRb signaling leading to withdrawal from the cell cycle. In an embodiment, the numbers of senescent and non-senescent cells present in the donor and/or receiver composition is determined. In some embodiments, a donor composition suitable for use in the present disclosure comprises or is modified to comprise less than about 20% senescent cells based on the total cell number present in the composition, alternatively less than about 15%, 12.5%, 10%, 9%, 8%, 7%, 6%, 5%, 4%, 3%, 2%, or 1%. In some embodiments, a donor composition suitable for use in the present disclosure comprises or is modified to comprise from about 80% to about 99% non-senescent cells, alternatively from about 90% to about 95% or alternatively from about 98% to about 99% based on the total number of cells in the composition. In an embodiment, the compositions (i.e., donor and receiver) are obtained following administration of G-CSF (e.g., NEUPOGEN®) to a subject and comprise stem cells of the type disclosed herein containing less than about 10% non-senescent cells based on the total number of cells obtained. Alternatively, less than about 9%, 8%, 7%, 6%, 5%, 4%, 3%, 2%, or 1% non-senescent cells based on the total number of cells obtained or alternatively from about 0.1% to about 10%, alternatively from about 0.1% to about 5% or alternatively from about 0.1% to about 1%.

In some embodiments, the donor composition and/or receiver composition may be utilized in the methodologies disclosed herein within 48 hours of obtaining the composition from the subject. In such embodiments, the compositions may be stored in a manner suitable for maintaining the viability of the composition until it is utilized. In alternative embodiments, the donor composition and/or receiver composition may be stored for some period of time prior to utilization of the composition in the methodologies disclosed herein. In such embodiments, the donor and/or receiver composition may be subjected to any suitable methodology for maintaining the viability of the composition until it is utilized. For example, cryopreservatives may be added to the composition and the composition stored at the appropriate temperatures, for example the sample may be initially stored at −4° C. and then later stored at −156° C. (liquid nitrogen vapor phase) or −196° C. (liquid nitrogen liquid phase). In an embodiment, the donor composition and/or receiver composition is stored for a period of time ranging from about 3 days to about 50 years, alternatively from about 1 month to about 50 years, alternatively from about 6 months to about 50 years, or alternatively greater than about 6 months before utilization of the composition.

In an embodiment, the ability of the donor composition to generate a composition useful for the restoring process disclosed herein may be assessed. Such assessments are termed "quality control methods." In an embodiment, a quality control method for the donor composition comprises measuring the level of expression of one or more genes or proteins for the cells of the donor composition. Herein the genes used to assess the quality of the donor composition are collectively referred to as the biomarker quality control panel comprising genes (BQCP-G) while proteins used to assess the quality of the donor composition are collectively referred to as the biomarker quality control panel comprising proteins (BQCP-P). For example, the BQCP-G may include but is not limited to genes associated with oxidative stress such as GPX-1 (encoding for glutathione peroxidase-1) and SOD1 (encoding for superoxide dismutase-1); genes associated with inflammation such as REL-A (encoding for p65 of the NFκB heterodimer); genes associated with DNA repair such as LIG-4 (encoding for DNA Ligase-4); senescence-associated genes such as GLB-1 (encoding for β—galactosidase) and, p16INK4a; or combinations thereof. The quality control method may yield a restoring quality value.

In an embodiment, the restoring quality value is correlated with the level of expression of one more the genes in the (e.g., BQCP-G) or proteins (BQCP-P) and may be assigned a value ranging from about 1 to about 10 where 1 denotes the least favorable pattern of gene expression and 10 denotes the most favorable pattern of gene expression. It is to be understood that the pattern of gene expression, and thus the restoring quality value, takes into account both (i) increases in the level of expression of genes and/or or proteins that favor cell function and viability and (ii) decreases in the level of expression of genes and/or proteins that are adverse to cellular function and viability. In an embodiment, a donor composition suitable for use in the present disclosure is characterized by a restoring quality value of from about 7 to about 10, alternatively greater than about 6, alternatively greater than about 8, alternatively greater than about 9, or alternatively 10.

It is to be understood that the restoring quality value reflects the restoring quality of the entire collection of cells present in the donor composition. It is contemplated that a particular sample of cells present in the donor composition may comprise a plurality of subpopulations having differing restoring quality values each contributing to the final determined value. For example, a donor composition may have a restoring quality value of 8, with the value being the result of 50% of the cells of the composition having a restoring quality value of 6 and 50% of the cells of the composition having a restoring quality value of 10. In some aspects these subpopulations may be identified and such information utilized to modify the donor composition such that the majority of cells in the composition (e.g., greater than about 70%) display improved restoring quality values.

In one embodiment, a methodology disclosed herein comprises the restoration of at least a portion of a receiver composition. Herein "restoration" refers to modification of a cell (e.g., stem cell) such that expression of one or more senescence-promoting agents is reduced and/or expression of one or more cell viability/cell function-promoting agents is increased. Without wishing to be limited by theory, the methodologies and compositions disclosed herein may result in the epigenetic modification of one or more cell types that results in at least one characteristic associated with improved cellular function when compared to an otherwise similar cell type not subjected to the compositions and methods disclosed herein. Herein "epigenetic" refers to the heritable changes in gene activity and expression that occurs without alternation in DNA sequence. Nonlimiting examples of epigenetic modifications include posttranslational modifications such as DNA methylation and chromatin remodeling and histone modification. Herein "improved cellular function" refers to characteristics such as an elevated level of expression of genes that promote cell viability, enhanced cell viability, and/or a reduced presence of materials detrimental to the functioning of the cell.

In an embodiment a schematic of a method for restoration of at least a portion of a subject's stem cells is depicted in FIG. 1. Referring to FIG. 1, a transwell chamber 100 comprises an upper well 10 with a permeable membrane 30 disposed within a lower well 20 which contains a receiver composition 50. In an embodiment, a method for restoration of at least a portion of a receiver composition 50 comprises the introduction a donor composition 40 to the upper well. The donor composition 40 and/or receiver composition 50 may be supplemented with one or more components of a culture media designed to maintain viability of the composition during the co-culturing of the donor composition 40 and receiver composition 50. The transwell may be incubated under suitable cell culture conditions for a time period ranging from about 1 hour to about 90 days, alternatively from about 24 hours to about 30 days, alternatively from about 48 hours to about 30 days, alternatively from about 72 hours to about 30 days, alternatively from about 96 hours to about 30 days, alternatively greater than about 24 hours, or alternatively from about 24 hours to about 60 days. The permeable membrane 30 of upper well 10 may be configured to a pore size sufficient to prohibit the passage of cells or cell-size material from the upper well 10 to the lower well 20 but permits the passage of smaller material, for example the permeable membrane 30 may have a 0.4 μm pore size. In an embodiment, during restoration the material that passes through the permeable membrane 30 and contacts the receiver composition 50 is termed the restoring composition 60.

In an alternative embodiment, the donor composition is cultured in a media independently of the receiver composition. In such embodiments, the donor composition may be cultured for a time period ranging from about 1 hour to about 90 days, alternatively from about 24 hours to about 30 days, alternatively from about 48 hours to about 30 days, alternatively from about 72 hours to about 30 days, alternatively from about 96 hours to about 30 days, alternatively greater than about 24 hours, or alternatively from about 24 hours to about 7 days. The cultured donor composition may then be subjected to any methodology suitable to separate the cells present in the composition from the media (e.g., centrifugation) and produce a cell-free media that may also be employed as a restoring composition. In such embodiments, the restoring composition may be contacted with the receiver composition using any suitable methodology, such as for example culturing the receiver composition in the restoring composition for a time period ranging from about 1 hour to about 30 days, alternatively from about 24 hours to about 30 days, alternatively from about 48 hours to about 30 days, alternatively from about 72 hours to about 30 days, alternatively from about 96 hours to about 30 days, alternatively greater than about 24 hours, or alternatively from about 24 hours to about 60 days.

It is contemplated that the restoring composition comprises material generated by the cells of the donor composition that are no longer associated with the cells and capable of passing through the permeable membrane in the case of the co-culturing method involving a transwell. In an embodiment, the restoring composition comprises secreted vesicles such as exosomes, microvesicles, cell-derived soluble vesicle compartments, cell-derived soluble factors, or combinations thereof.

In an embodiment, during the time period in which the receiver composition is contacted with the restoring composition, one or more analytical methods may be employed to determine the functioning and/or viability of the cells present in the receiver composition, the donor composition, or both. For example, the cellular viability of the cells present in the donor and/or receiver composition may be assayed by a colony forming assay; and/or alterations in the gene expression or protein expression patterns of the cells. In an embodiment, the gene expression patterns of the cells present in the donor and/or receiver compositions may be assessed using gene expression arrays. Herein gene expression arrays refer to supports upon which a collection of gene-specific nucleic acids have been placed at defined locations, either by spotting or direct synthesis. In array analysis, a nucleic acid-containing sample is labeled and then allowed to hybridize with the gene-specific targets on the array. In an embodiment, the gene array comprises nucleic acids specific for senescence-associated genes. For example and without limitation, alterations in the expression of genes such as telomerase, GPX1, SOD, RELA, LIG4, P16ink4a, and GLB1 in the donor composition and/or receiver composition as a result of the restoration method may be determined. Protein expression may be assessed using any suitable methodology such as protein arrays or via immunoassays.

In an embodiment, the receiver composition once contacted with the restoring composition for some period of time functions to restore the cellular function of at least a portion of the cells present in the receiving composition. Cells present in the receiver composition displaying improved cellular function subsequent to contact with the restoring composition are termed restored cells. Restored cells may display increased cellular viability as determined by cellular viability assays such as the colony-forming unit assay, trypan blue exclusion assays and/or decreased cellular senescence as associated by a reduction in the expression of senescence-associated genes or an increase in the expression of genes associated with improved cellular function. For example, the restored cells may exhibit a decrease in the secretion of proinflammatory cytokines, chemokines, growth factors and proteases typically associated with senescent cells. In an embodiment, the restored cells display increased cell viability and functionality, reduced expression of senescence markers, increased mitochondrial function, reduced expression of inflammatory genes, increased expression of DNA repair genes, or combinations thereof when compared to the receiver composition. In an embodiment, the restored cells exclude induced pluripotent cells.

It is contemplated that the receiver composition contacted with a restoring composition of the type disclosed herein contains soluble or otherwise incorporated agents originating from the donor composition. The cells of the receiver composition whose cellular function can be altered by contact with the restoring composition, i.e. restored, are termed restorable cells. In an embodiment, the receiver composition contains greater than about 5% restorable cells, alternatively greater than about 10% restorable cells, alternatively greater than about 50% restorable cells, or alternatively from about 5% to about 80% restorable cells.

In an embodiment, the restored cells may be formulated for administration to a subject in need thereof. In an embodiment, the subject is the receiver subject. For example, the restored cells may be a component of a formulation that is administered to the receiver subject to improve the receiver's subject's general health. Such improvements may be identified by quantitative evaluation of one or more physiological or psychological parameters. In the alternative such improvements may be identified by the qualitative evaluations of one or more physiological or psychological parameters. In an embodiment, the receiver subject is prophylactically administered the restored cells.

In an alternative embodiment the receiver subject is administered the restored cells as a component of a therapeutic procedure designed to ameliorate the effects of a medical condition. In such embodiments the restored cells, present in a therapeutically effective amount, may function as an active agent in a pharmaceutical composition. Such pharmaceutical compositions comprising restored cells are hereinafter termed cell-based pharmaceutical compositions or CBPC. Additional actives may be present in the CBPC as considered beneficial for the treatment of the medical condition. Examples of additional actives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; and (h) combinations thereof. Such additional actives may also be present in a therapeutically effective amount.

Examples of additional actives for inclusion in the CBPC pharmaceutical or drug include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor.

Specific compounds suitable for use in the CBPC include silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), NEOSPORIN® (i.e., Bacitracin, Polymyxin B, and Neomycin), POLYSPORIN® (i.e., Bacitracin and Polymyxin B). Additional antimicrobials include topical antimicrobials (i.e., antiseptics), examples of which include silver salts, iodine, benzalkonium chloride, alcohol, hydrogen peroxide, chlorhexidine, acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin, Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol;

Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Eeadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Tiernafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine, Alclofenac; Alclometasone Dipropionate; Algestone Acetonide; Alpha Amylase; Ameinafal; Ameinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

In an embodiment, the CBPC may contain additional ingredients as suitable for the formulation of a pharmaceutical composition. As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials.

Generally, the CBPC may be administered systemically, for example, orally, parenterally, or via intravenous administration in dosage unit formulations containing conventional nontoxic pharmaceutically acceptable carriers, adjuvants, and vehicles as desired, or may be locally administered by means such as, but not limited to, injection, implantation, grafting or parenterally. A means of administering the CBPC may include, but is not limited to, infusion. Systemically may also include, for example, by a pump, by an intravenous line, or by bolus injection. Bolus injection can include subcutaneous, intramuscular, or intraperitoneal routes. The phrases "systemic administration" or "administered systemically" as used herein mean the administration of a compound(s) of the disclosure, composition, drug or other material, such that it enters the subject's system and, thus, is subject to metabolism and other like processes, for example, subcutaneous administration.

Although the descriptions of pharmaceutical (CBPC) and prophylactic compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals can be accomplished by the ordinarily skilled veterinary pharmacologist, with the benefit of this disclosure, who can design and perform such modifications with routine, if any, experimentation. Subjects to which administration of the pharmaceutical compositions of this disclosure is contemplated include, but are not limited to, humans and other primates, mammals including commercially relevant mammals such as cattle, pigs, horses, sheep, cats, and dogs, and birds including commercially relevant birds such as chickens, ducks, geese, and turkeys.

In certain embodiments, a therapeutically effective dose of the CBPC is delivered to the subject. A therapeutically effective dose will be determined by the body weight of the subject receiving treatment, and may be further modified, for example, based on the severity or phase of the medical condition. The number of cells used will depend on the weight and condition of the receiver subject the number of or frequency of administrations, and other variables. For example, a therapeutic dose may be one or more administrations of the CBPC.

In an embodiment, the restored cells are formulated for topical administration into forms such as creams, lotions, serums, powders, ointments or drops. A formulation of restored cells for topical administration may also contain pharmaceutically acceptable carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or UV-blockers, antibacterials, antifungals, disinfectants, vitamins, antibiotics, anti-acne agents, as well as other suitable materials that do not have a significant adverse effect on the activity of the topical composition. Nonlimiting exemplary pharmaceutically acceptable carriers that may be used in the compositions comprising the restored cells may include water, mixtures of water and water-miscible solvents such as lower alkanols or vegetable oils, and water-soluble ophthalmologically acceptable non-toxic polymers (for example, cellulose derivatives such as methylcellulose), glycerin, propylene glycol, methylparaben, alginates, glyceryl stearate, PEG-100 stearate, cetyl alcohol, propylparaben, butylparaben, sorbitols, polyethoxylated anhydrosorbitol monostearate (TWEEN®), white petrolatum (VASELINE®), triethanolamine, emu oil, aloe vera extract, lanolin, cocoa butter, LIPODERM® base, and the like. In an embodiment, the restored cells formulated for topical administration may be applied to one or more areas of the skin including the face, hands and neck.

In an embodiment the methodologies disclosed herein result in therapies that are prophylactic, palliative, curative, or combinations thereof. Methodologies and compositions of the type disclosed herein may be utilized in the treatment of a wide variety of undesirable conditions related to decreases in cellular function and viability such as age-related undesirable conditions such as neurological disorders; autoimmune diseases; and disorders associated with radiation overexposure (chronic or acute).

It is contemplated the methodologies and compositions disclosed herein may result in an increased expression of genes associated with beneficial cellular events with a concomitant decrease in the expression of genes associated with adverse cellular events. In some embodiments, the methodologies and compositions disclosed herein result in an increased expression of genes associated with beneficial cellular events.

EXAMPLES

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims. The examples are given as a more detailed demonstration of some of the aspects and embodiments described herein and are not intended to limit the disclosure or claims in any manner.

Example 1

Figure 6:
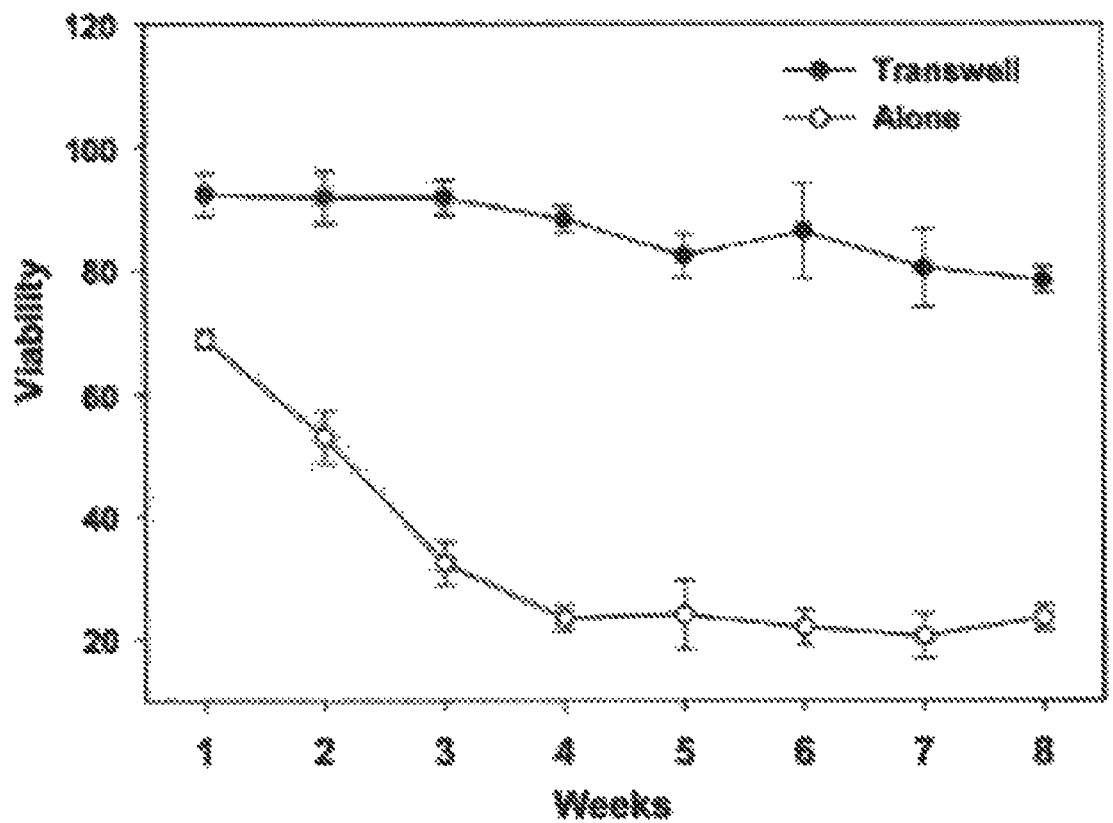
FIG. 6 depicts a plots of the cellular viability over a time period of eight weeks for samples from Example 1 having in the absence of exposure to a restoring composition (designated alone) or having been exposed to a restoring composition (designated transwell).
Figure 7:
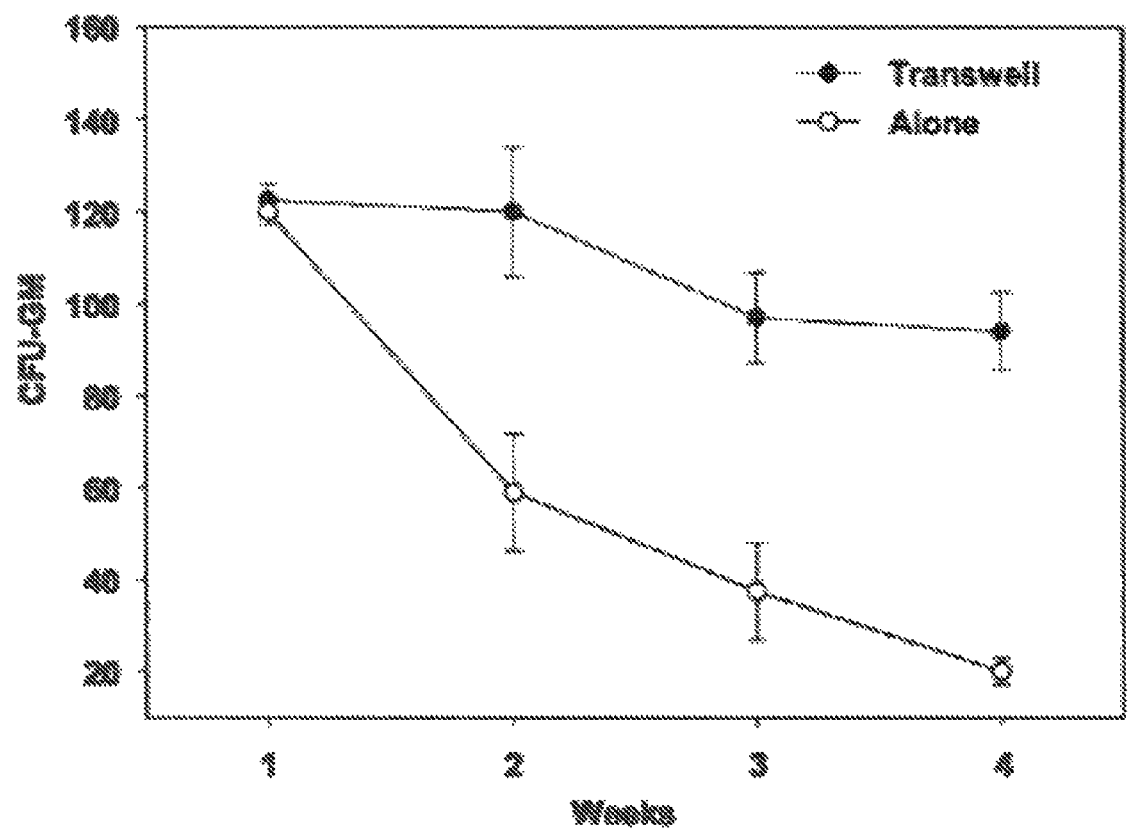
FIG. 7 depicts a plots of the cellular viability for samples from Example 1 having in the absence of exposure to a restoring composition (designated alone) or having been exposed to a restoring composition (designated transwell) for the first through fourth weeks of an eight week experiment.
Figure 8:
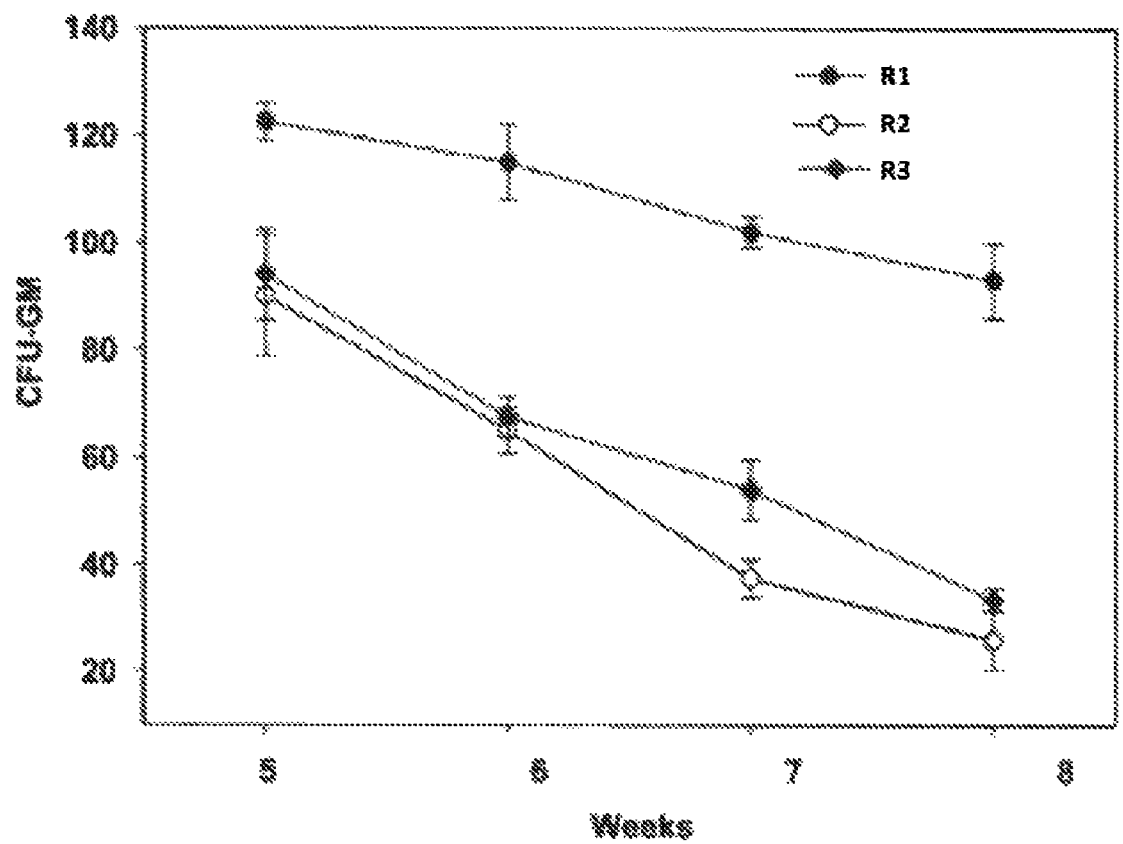
FIG. 8 depicts plots of the cellular viability for samples of the receiver subjects from Example 1 having been exposed to a restoring composition for the fifth through eighth weeks of an eight week experiment.

Five compositions of the type disclosed herein were obtained from five subjects. Subjects R1, R2, and R3 were receiver subjects who were greater than 60 years in age. Subjects D1 and D2 were donor subjects who were less than 30 years old at the time the compositions were obtained. The compositions were obtained from the subjects post mobilization with NEUPOGEN and standard protocols were utilized for obtaining the compositions. The quality of the compositions obtained were analyzed by flow cytometry and clonogenic assays utilizing standard protocols. The results of these analyses are presented in FIGS. 2a-5b. Transwell experiments of the type disclosed herein were conducted and donor compositions were placed in the upper chamber of a transwell assembly while receiver compositions were placed in the lower chamber and the compositions observed for eight weeks. FIGS. 6 and 7 display typical plots observed when the cell viability was monitored as a function of time for receiver composition (designated alone) and the receiver composition exposed to a donor composition (designated transwell). Plots of the cell proliferation between the fifth and eighth weeks for the receiver compositions are displayed in FIG. 8.

Example 2

Figure 9:
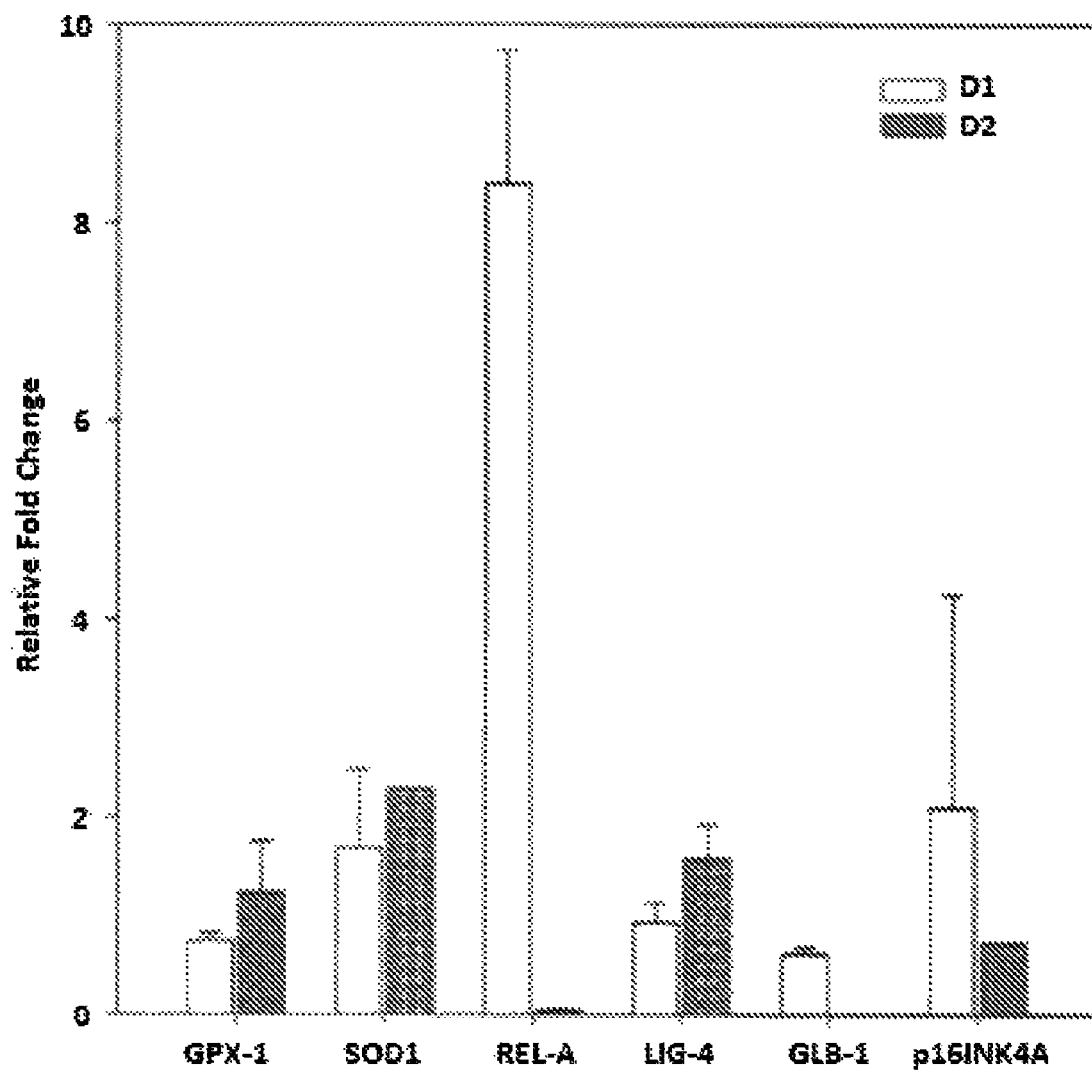
FIG. 9 depicts a plot of the relative change in gene expression for the indicated genes of the donor subjects in Examples 1 and 2.
Figure 10A:
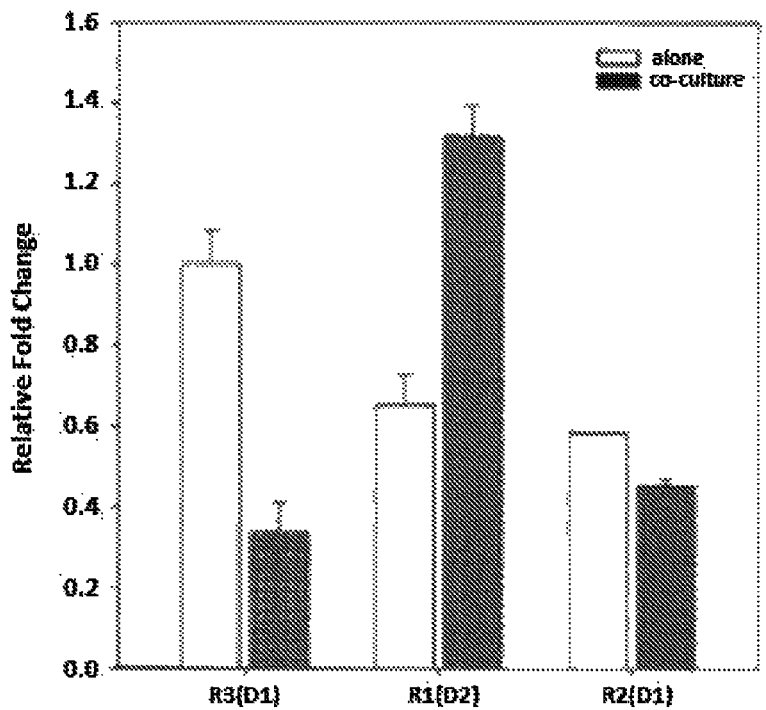
FIG. 10a depicts a plot of the relative changes in expression of the glutathione peroxidase gene (GPX-1) for receiver compositions cultured alone (designated alone) or co-cultured with donor compositions (designated co-culture) for the samples of Example 1.
Figure 10B:
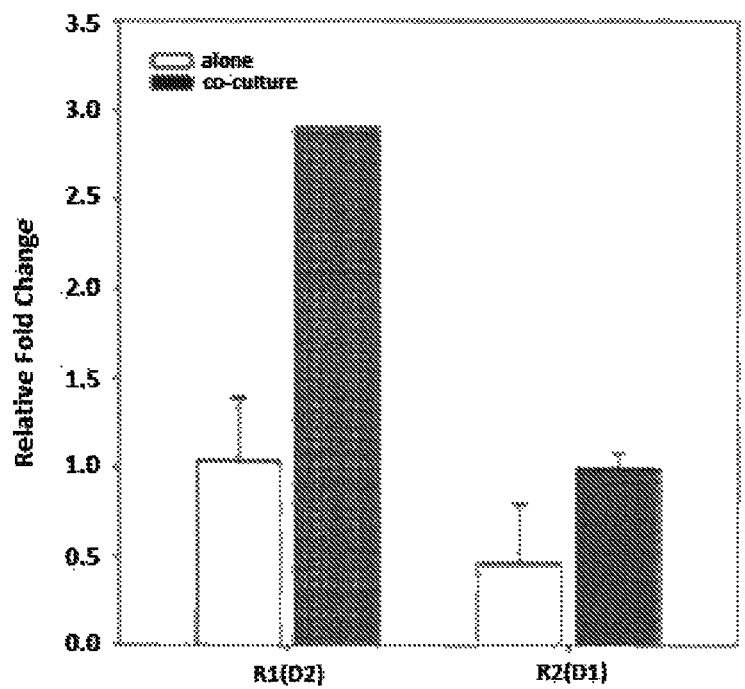
FIG. 10b depicts a plot of the relative changes in expression of the superoxide dismutase gene (SOD-1) for receiver compositions cultured alone (designated alone) or co-cultured with donor compositions (designated co-culture) for the samples of Example 1.
Figure 11A:
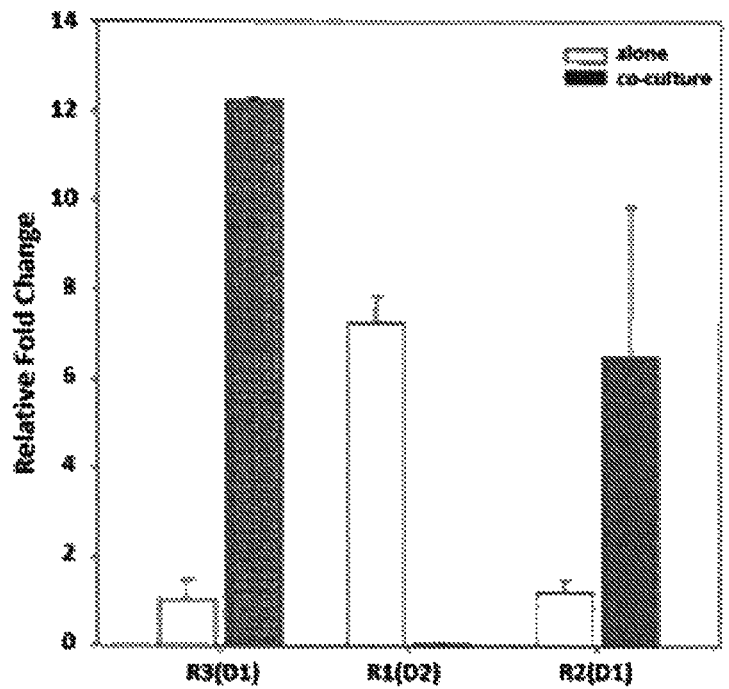
FIG. 11a depicts a plot of the relative changes in expression of the RELA-A gene for receiver compositions cultured alone (designated alone) or co-cultured with donor compositions (designated co-culture) for the samples of Example 1.
Figure 11B:
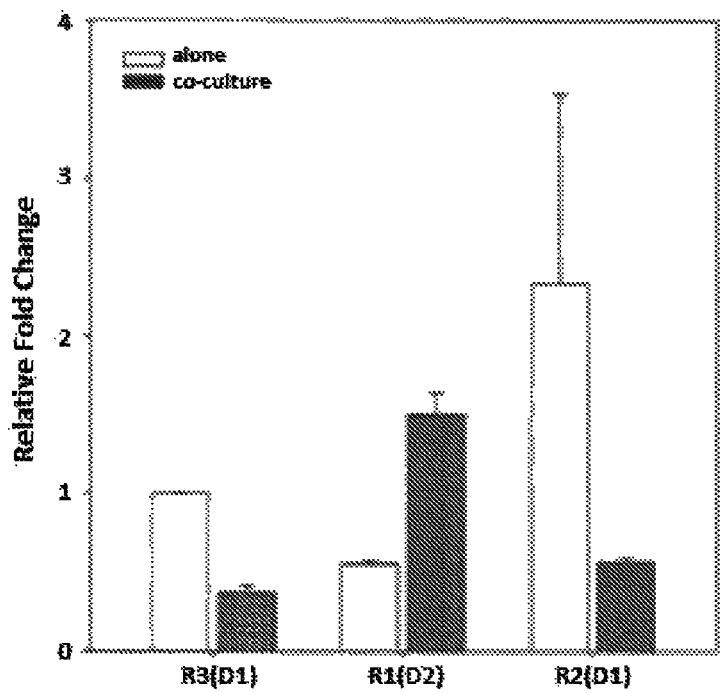
FIG. 11b depicts a plot of the relative changes in expression of the LIG-1 gene for receiver compositions cultured alone (designated alone) or co-cultured with donor compositions (designated co-culture) for the samples of Example 1.
Figure 12A:
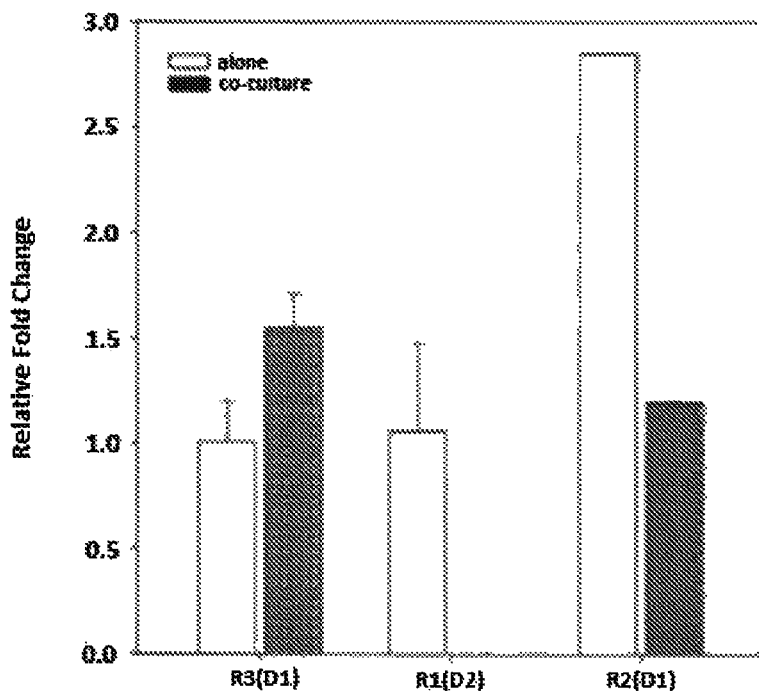
FIG. 12a depicts a plot of the relative changes in expression of the GLB-1 gene for receiver compositions cultured alone (designated alone) or co-cultured with donor compositions (designated co-culture) for the samples of Example 1.
Figure 12B:
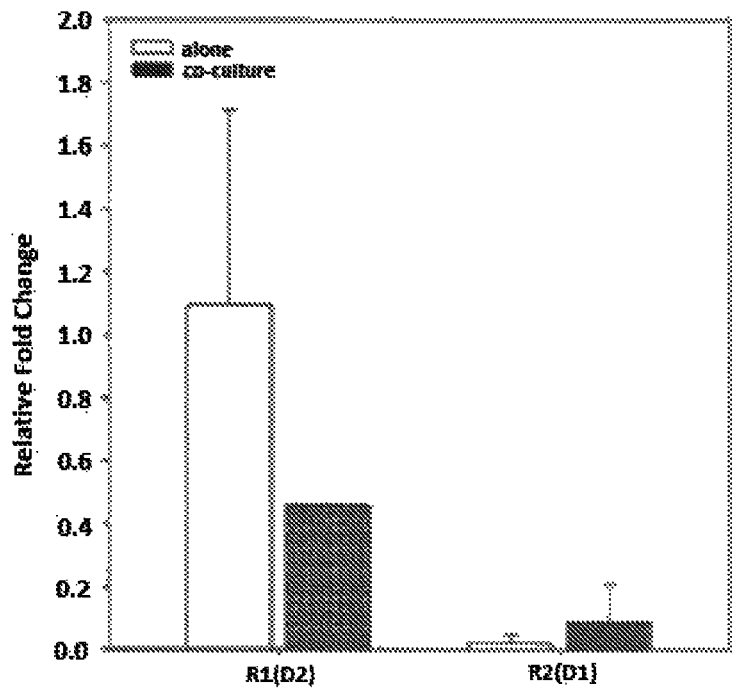
FIG. 12b depicts a plot of the relative changes in expression of the CDKN2A gene for receiver compositions cultured alone (designated alone) or co-cultured with donor compositions (designated co-culture) for the samples of Example 1.
Figure 13A:
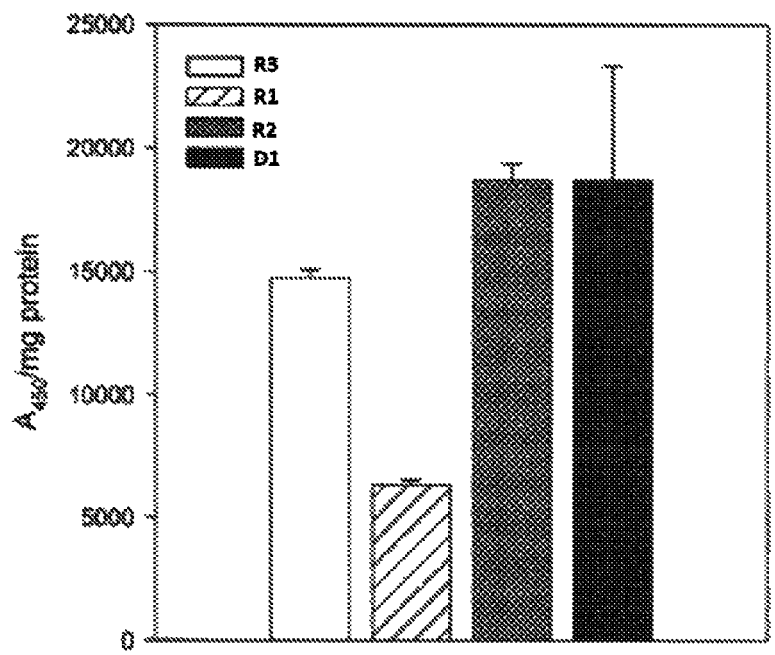
FIG. 13a depicts a plot of the teleomerase activity for the samples from Example 1 prior to being subjected to a restoration process of the type disclosed herein.
Figure 13B:
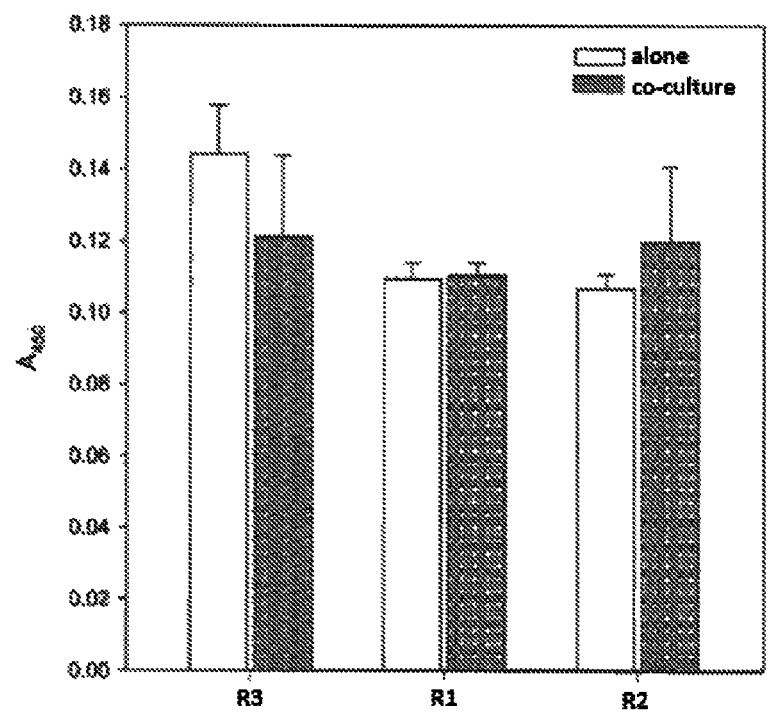
FIG. 13b depicts the change in telomerase activity for the receiver subjects of Example 1 cultured alone (designated alone) or co-cultured with donor compositions (designated co-culture).

The level of expression of various genes in both donor and receiver compositions were determined using standard protocols. FIG. 9 is a plot of the relative fold change in gene expression of the genes between the two donor subjects D1 and D2. FIGS. 10a-12b plot the relative fold change in expression of the indicated gene, for the receiver compositions prior to exposure to a donor composition (alone) and subsequent to the transwell experiment described in Example 1 (designated co-culture). The teleomerase activity of the indicated compositions were assayed using standard protocols such as the TRAP or modified TRAP protocol and these results are presented in FIGS. 13a and 13b.

Additional Disclosure

The following are enumerated embodiments which are provided as non-limiting examples:

A first embodiment which is a method comprising obtaining a donor composition from a donor subject wherein the donor composition comprises a plurality of adult stem cell types; obtaining a receiver composition from a receiver subject wherein the receiver composition comprises a plurality of adult stem cell types; and co-culturing the donor composition and receiver composition wherein co-culturing comprises contacting the receiver composition with a cell-free portion of the donor composition to produce a restored composition.

A second embodiment which is the method of the first embodiment wherein the adult stem cell types comprise mesenchymal stem cells, hematopoietic stem cells, early hematopoietic progenitor cells, late hematopoietic progenitor cells, endothelial progenitor cells or combinations thereof.

A third embodiment which is the method of any of the first through second embodiments further comprising administering to the donor subject, the receiver subject, or both a mobilizer prior to obtaining the donor composition or receiver composition.

A fourth embodiment which is the method of the third embodiment wherein the mobilizer comprises a small organic molecule, synthetic or naturally derived, or a polypeptide, such as a growth factor or colony stimulating factor or an active fragment or mimic thereof, a nucleic acid, a carbohydrate, an antibody, or combinations thereof.

A fifth embodiment which is the method of any of the third through fourth embodiments wherein the mobilizer comprises granulocyte colony-stimulating factor.

A sixth embodiment which is the method of any of the first through fifth embodiments further comprising subjecting the donor subject, the receiver subject, or both to one or more methods to improve the subject's general health prior to obtaining the donor composition, the receiver composition, or both.

A seventh embodiment which is the method of the sixth embodiment wherein the one or more methods to improve the subject's general health comprises administration of metabolic mediators, administration of a pulsed electromagnetic field, or combinations thereof.

An eighth embodiment which is the method of the seventh embodiment wherein the metabolic mediator comprises a nutraceutical.

A ninth embodiment which is the method of any of the sixth through eighth embodiments wherein the method to improve the subject's general health are carried out for at time period ranging from about 48 hours to about 1 year prior to obtaining the donor composition, the receiver composition, or both.

A tenth embodiment which is the method of any of the first through ninth embodiments wherein the donor composition, the receiver composition, or both are obtained from a bone marrow of the subject.

An eleventh embodiment which is the method of any of the first through tenth embodiments further comprising analyzing the quality of the donor composition, the receiver composition, or both.

A twelfth embodiment which is the method of the eleventh embodiment wherein analyzing the quality of the donor composition, the receiver composition or both comprises subjecting the composition to flow cytometry analysis, clonogenic assays, cell viability assays, or combinations thereof.

A thirteenth embodiment which is the method of any of the first through twelfth embodiments wherein the donor composition, the receive composition, or both comprise senescent and non-senescent cells.

A fourteenth embodiment which is the method of the thirteenth embodiment wherein the donor composition, the receiver composition or both comprise less than about 20% senescent cells based on the total number of cells in the composition.

A fifteenth embodiment which is the method of any of the first through fourteenth embodiments wherein the donor subject and the receiver subject are the same.

A sixteenth embodiment which is the method of any of the first through fifteenth embodiments wherein the donor subject and the receiver subject are different.

A seventeenth embodiment which is the method of any of the first through sixteenth embodiments wherein the donor subject and the receiver subject are related by consanguinity.

An eighteenth embodiment which is the method of any of the first through seventeenth embodiments wherein the donor subject and receiver subject differ in age by from about 5 years to about 75 years.

A nineteenth embodiment which is the method of any of the first through eighteenth embodiments wherein the donor composition excludes embryonic material or material derived from embryonic or fetal tissue.

A twentieth embodiment which is the method of any of the first through nineteenth embodiments further comprising formulating the restored composition for administration to a subject.

A twenty-first embodiment which is the method of any of the first through twentieth embodiments wherein the restored composition is formulated with a pharmaceutically active compound.

A twenty-second embodiment which is the method of the twenty-first embodiment wherein the pharmaceutically active compound comprises antimicrobials, steroids, pain medications, anti-inflammatory agents, growth factors, cytokines, hormones or combinations thereof.

A twenty-third embodiment which is the method of any of the twenty-first through twenty-second embodiments wherein the pharmaceutically active compound comprise anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitors or combinations thereof.

A twenty-fourth embodiment which is the method of any of the first through twenty-third embodiments wherein the restored composition comprises cells that display an altered expression of at least one gene selected from the group consisting of GPX-1 (encoding for glutathione peroxidase-1), SOD1 (encoding for superoxide dismutase-1); REL-A (encoding for p65 of the NFκB heterodimer); LIG-4 (encoding for DNA Ligase-4); GLB-1 (encoding for β-galactosidase) and, p16INK4a.

A twenty-fifth embodiment which is the method of any of the first through twenty-fourth embodiments wherein the restored composition excludes induced pluripotent cells.

A twenty-sixth embodiment which is the method of any of the first through twenty-fifth embodiments wherein the receiver subject has a medical condition that is absent from or undiagnosed in the donor subject.

A twenty-seventh embodiment which is a pharmaceutical composition comprising the restored composition of any of the first through twenty-sixth embodiments.

A twenty-eighth embodiment which is the restored composition of any of the first through twenty-sixth embodiments.

A twenty-ninth embodiment which is the cell-free portion of the donor composition of any of the first through twenty-sixth embodiments.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

What is claimed is:

1. A method of restoring adult stem cells comprising:
   obtaining a donor composition from a donor subject wherein the donor composition comprises a plurality of adult stem cell types;
   obtaining a receiver composition from a receiver subject wherein the receiver composition comprises a plurality of adult stem cell types and wherein the donor subject and receiver subject differ in chronological age by from about 5 years to about 75 years;
   culturing the donor composition in a media for a time period ranging from about 1 hour to about 90 days wherein culturing the donor composition results in the production of secreted vesicles, microvesicles, cell-derived soluble vesicle compartments, cell-derived soluble factors, or a combination thereof;
   separating the adult stem cell types in the donor composition from the media to produce a cell-free donor composition wherein separating comprises filtering the cells in the donor composition through a permeable membrane; and
   co-culturing the cell-free donor composition and receiver composition wherein co-culturing comprises contacting the receiver composition with the cell-free donor composition to produce a restored composition wherein the restored composition comprises cells that display an altered expression of at least one gene selected from the group consisting of GPX-1 (encoding for glutathione peroxidase-1), SOD 1 (encoding for superoxide dismutase-1); REL-A (encoding for p65 of the NFKB heterodimer); LIG-4 (encoding for DNA Ligase-4); GLB-1 (encoding for —galactosidase) and p16INK4 and wherein the altered expression comprises a change in the expression level of the at least one gene of at least 1.5 fold.

2. The method of claim 1 wherein the adult stem cell types comprise mesenchymal stem cells, hematopoietic stem cells, early hematopoietic progenitor cells, late hematopoietic progenitor cells, endothelial progenitor cells or combinations thereof.

3. The method of claim 1 further comprising administering to the donor subject, the receiver subject, or both a mobilizer prior to obtaining the donor composition, the receiver composition or both.

4. The method of claim 3 wherein the mobilizer comprises a synthetically-derived small organic molecule, a naturally-derived small organic molecule, a polypeptide, a growth factor, a colony-stimulating factor or an active fragment or mimic thereof, a nucleic acid, a carbohydrate, an antibody, or combinations thereof.

5. The method of claim 3 wherein the mobilizer comprises granulocyte colony-stimulating factor.

6. The method of claim 1 further comprising subjecting the donor subject, the receiver subject, or both to one or more methods to improve the subject's general health prior to obtaining the donor composition, the receiver composition, or both.

7. The method of claim 6 wherein the one or more methods to improve the subject's general health comprises administration of metabolic mediators, administration of a pulsed electromagnetic field, or combinations thereof.

8. The method of claim 7 wherein the metabolic mediator comprises a nutraceutical.

9. The method of claim 6 wherein the method to improve the subject's general health are carried out for at time period ranging from about 48 hours to about 1 year prior to obtaining the donor composition, the receiver composition, or both.

10. The method of claim 1 wherein the donor composition, the receiver composition, or both are obtained from a bone marrow of the subject.

11. The method of claim 1 further comprising analyzing the quality of the donor composition, the receiver composition, or both.

12. The method of claim 11 wherein analyzing the quality of the donor composition, the receiver composition or both comprises subjecting the composition to flow cytometry analysis, clonogenic assays, cell viability assays, or combinations thereof.

13. The method of claim 1 wherein the donor composition, the receiver composition, or both comprise senescent and non-senescent cells.

14. The method of claim 13 wherein the donor composition, the receiver composition or both comprise less than about 20% senescent cells based on the total number of cells in the composition.

15. The method of claim 1 wherein the donor subject and the receiver subject are the same.

16. The method of claim 1 wherein the donor subject and the receiver subject are different.

17. The method of claim 1 wherein the donor subject and the receiver subject are related by consanguinity.

18. The method of claim 1 wherein the donor composition excludes embryonic material or material derived from embryonic or fetal tissue.

19. The method of claim 1 further comprising formulating the restored composition for administration to a subject.

20. The method of claim 19 wherein the restored composition is formulated with a pharmaceutically active compound.

21. The method of claim 20 wherein the pharmaceutically active compound comprises antimicrobials, steroids, pain medications, anti-inflammatory agents, growth factors, cytokines, hormones or combinations thereof.

22. The method of claim 20 wherein the pharmaceutically active compound comprise anesthetics, hypnotics, sedatives and sleep inducers, anti-psychotics, antidepressants, antiallergics, antianginals, antiarthritics, antiasthmatics, antidiabetics, antidiarrheal drugs, anticonvulsants, anti-gout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, antioxidants, vitamins, cosmetics, antiinflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitors or combinations thereof.

23. The method of claim 1 wherein the restored composition excludes induced pluripotent cells.

24. The method of claim 1 wherein the receiver subject has a medical condition that is absent from or undiagnosed in the donor subject.

* * * * *